United States Patent
Degtiarenko et al.

(10) Patent No.: US 7,279,882 B1
(45) Date of Patent: Oct. 9, 2007

(54) METHOD AND APPARATUS FOR MEASURING PROPERTIES OF PARTICLE BEAMS USING THERMO-RESISTIVE MATERIAL PROPERTIES

(75) Inventors: Pavel V. Degtiarenko, Williamsburg, VA (US); Danny Wayne Dotson, Gloucester, VA (US)

(73) Assignee: Jefferson Science Associates, LLC, Newport News, VA (US)

( * ) Notice: Subject to any disclaimer, the term of this patent is extended or adjusted under 35 U.S.C. 154(b) by 519 days.

(21) Appl. No.: 10/957,763

(22) Filed: Oct. 4, 2004

(51) Int. Cl.
*G01N 27/00* (2006.01)
*A61N 5/00* (2006.01)
*H01J 3/14* (2006.01)

(52) U.S. Cl. ............ 324/71.3; 250/492.3; 250/397
(58) Field of Classification Search ............ 324/71.3, 324/71.1, 76.11, 158.1; 250/396 R, 397, 250/492.3, 206.1, 206.2, 370.1
See application file for complete search history.

(56) References Cited

U.S. PATENT DOCUMENTS

| | | | | |
|---|---|---|---|---|
| 3,733,546 A | * | 5/1973 | Faltens et al. | 324/71.1 |
| 4,060,762 A | * | 11/1977 | McKeown | 324/71.1 |
| 5,444,758 A | * | 8/1995 | Miyake et al. | 378/113 |
| 5,459,393 A | * | 10/1995 | Tanaka et al. | 324/71.3 |
| 5,631,461 A | * | 5/1997 | Swenson | 250/251 |
| 5,717,214 A | * | 2/1998 | Kitamura et al. | 250/370.1 |
| 5,939,704 A | * | 8/1999 | Perrie et al. | 250/201.1 |
| 6,573,497 B1 | * | 6/2003 | Rangarajan et al. | 250/306 |
| 6,617,596 B1 | * | 9/2003 | Korenev | 250/492.3 |
| 6,873,123 B2 | * | 3/2005 | Marchand et al. | 315/502 |
| 6,914,253 B2 | * | 7/2005 | Korenev et al. | 250/492.3 |
| 6,972,551 B2 | * | 12/2005 | Havener et al. | 324/71.3 |
| 2002/0121889 A1 | * | 9/2002 | Larsen et al. | 324/71.3 |

\* cited by examiner

*Primary Examiner*—Andrew H. Hirshfeld
*Assistant Examiner*—Hoai-An D. Nguyen (57) ABSTRACT

A beam position detector for measuring the properties of a charged particle beam, including the beam's position, size, shape, and intensity. One or more absorbers are constructed of thermo-resistive material and positioned to intercept and absorb a portion of the incoming beam power, thereby causing local heating of each absorber. The local temperature increase distribution across the absorber, or the distribution between different absorbers, will depend on the intensity, size, and position of the beam. The absorbers are constructed of a material having a strong dependence of electrical resistivity on temperature. The beam position detector has no moving parts in the vicinity of the beam and is especially suited to beam areas having high ionizing radiation dose rates or poor beam quality, including beams dispersed in the transverse direction and in their time radio frequency structure.

20 Claims, 10 Drawing Sheets

METHOD AND APPARATUS FOR MEASURING PROPERTIES OF PARTICLE BEAMS USING THERMO-RESISTIVE MATERIAL PROPERTIES

The United States of America may have certain rights to this invention under Management and Operating contract No. DE-AC05-84ER 40150 from the Department of Energy.

FIELD OF THE INVENTION

This invention relates to beam position detectors and specifically to an apparatus and method for measuring the position, size, shape, and intensity of a particle beam in a particle accelerator or light-generating device.

BACKGROUND OF THE INVENTION

When studying the behavior of charged particles at relativistic speeds, such as in particle accelerators, it is necessary and advantageous to measure the properties of the charged particle beam, including beam position, size, shape, and intensity. In a particle accelerator, this task becomes extremely challenging in those areas that have poor beam quality, such as in the vicinity of power beam dumps, which absorb the beam after it has been utilized in experimental targets or material treatment facilities. In these areas, as a result of the particle beam being dispersed by the targets or the treated materials, the quality of the beam is typically very poor. The beam is typically degraded in both the transverse direction and in its time radio frequency (RF) structure. In addition, the areas close to the beam dumps typically experience very high ionizing radiation dose rates from the dumps, and any equipment positioned there must be extremely resistant to radiation damage.

Several U.S. patents disclose apparatus and methods for measuring various properties of particle beams. However, each of these prior art patents either need good RF quality of the beam and small aperture, or need to implement moving parts and respective control systems that are difficult to maintain in working condition in the high radiation environment.

Therefore, what is needed is an apparatus and method for measuring the properties of a charged particle beam in high radiation areas and in areas in which the beam quality is poor.

SUMMARY OF THE INVENTION

The invention is a beam position detector for measuring the properties of a charged particle beam, including the beam's position, size, shape, and intensity. The beam position detector includes one or more absorbers constructed of thermo-resistive material and positioned to intercept and absorb a portion of the incoming beam power. Absorbing a portion of the incoming beam power causes local heating of each absorber. The local temperature increase distribution across the absorber, or the distribution between different absorbers, will depend on the intensity, size, and position of the beam. By constructing the absorbers of a material having a strong dependence of electrical resistivity on temperature and measuring the electrical resistance distribution across the absorber or between different absorbers, a beam position detector is constructed that is capable of measuring beam properties such as beam position, size, shape, and intensity. The absorbers are preferably in the form of rectangular plates or wires constructed of chemical vapor deposition silicon carbide.

OBJECTS AND ADVANTAGES

The beam position detector of the present invention provides a method of measuring particle beam properties in areas in which the quality of the beam is very poor, such as in the vicinity of beam dumps. In these areas the beam is dispersed in both the transverse direction and in its time RF structure and present methods of beam property measurement are inadequate to properly monitor the beam.

A further advantage of the beam position detector of the present invention is that it is highly resistant to radiation damage, and therefore may be used in areas, which exhibit very high ionizing radiation dose rates.

Another advantage of the beam position detector of the present invention is that it does not employ any moving parts, which would be difficult to maintain in an area susceptible to high ionizing radiation dose rates.

These and other objects and advantages of the present invention will be better understood by reading the following description along with reference to the drawings.

TABLE OF NOMENCLATURE

The following is a listing of part numbers used in the drawings along with a brief description:

| Part Number | Description |
|---|---|
| 20 | beam position detector |
| 22 | first absorber |

-continued

| Part Number | Description |
|---|---|
| 22A | first end on first absorber |
| 22B | second end on first absorber |
| 24 | second absorber |
| 24A | first end on second absorber |
| 24B | second end on second absorber |
| 26 | beam path |
| 30 | first current monitor |
| 32 | second current monitor |
| 34 | third current monitor |
| 36 | fourth current monitor |
| 38 | first voltage monitor |
| 40 | second voltage monitor |
| 42 | electrical leads to first absorber |
| 44 | electrical leads to second absorber |
| 50 | beam position detector (first alternate embodiment) |
| 52 | metallic conductor |
| 60 | beam position detector (second alternate embodiment) |
| 62 | first vertical absorber |
| 64 | second vertical absorber |
| 66 | first horizontal absorber |
| 68 | second horizontal absorber |
| A | current monitor or ammeter |
| V | voltage monitor or voltmeter |

DETAILED DESCRIPTION OF THE INVENTION

The present invention comprises a beam position detector for measuring the position, size, shape, and intensity of a charged particle beam.

Figure 1:
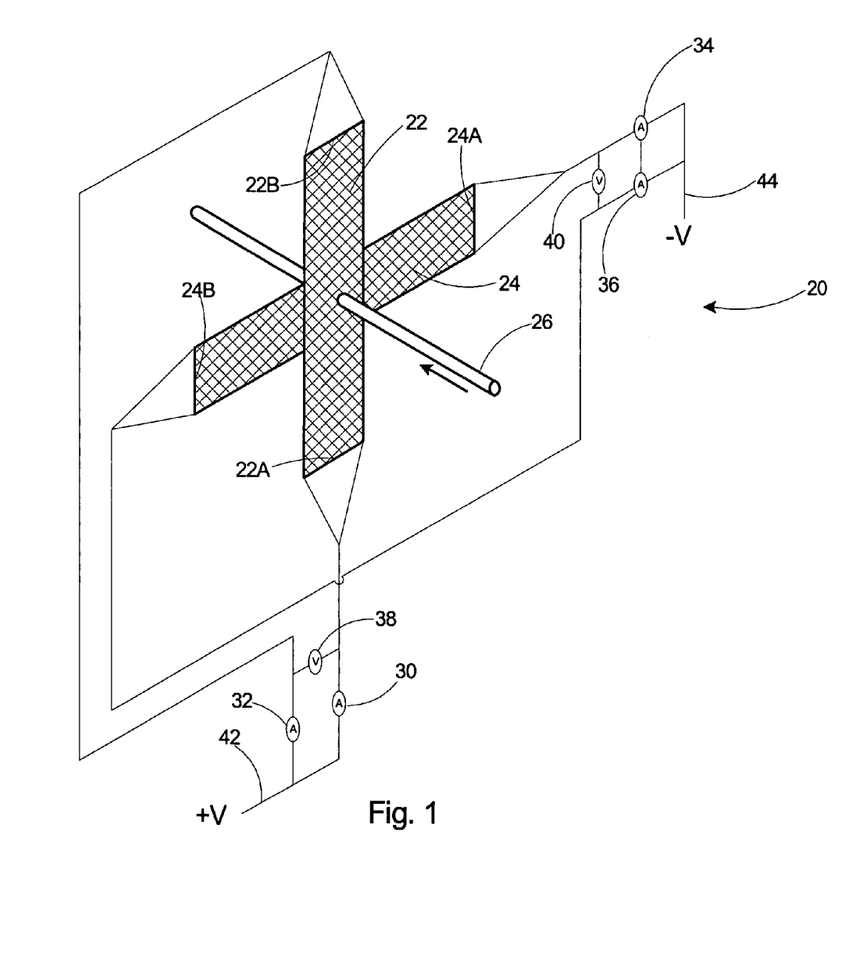
FIG. 1 is a perspective view of a preferred embodiment of a Beam Position Detector (BPD) according to the present invention using two resistive absorbers.

With reference to FIG. 1, the beam position detector 20 includes a first absorber 22 and a second absorber 24 positioned to intercept the incoming beam path 26. The absorbers 22, 24 may be in the form of plates, as shown in FIG. 1, or wires. The first absorber 22 is positioned vertically and orthogonal with respect to the path 26. The second absorber 24 is placed farther down the beam path 26 and is positioned horizontally and orthogonal with respect to the path 26. Each absorber 22, 24 has ends including ends 22A and 22B on the first absorber 22 and ends 24A and 24B on the second absorber 24. The beam position detector 20 includes a current monitor A at the ends of each of the absorbers 22, 24. A first current monitor 30 measures the current at the first end 22A of absorber 22 and a second current monitor 32 measures the current at the second end 22B of absorber 22. A third current monitor 34 measures the current at the first end 24A of absorber 24 and a fourth current monitor 36 measures the current at the second end 24B of absorber 24. Voltage meters V measure the voltage across each of the absorbers, including a first voltage monitor 38 measuring the voltage across absorber 22 and a second voltage monitor 40 measuring the voltage across absorber 24. To charge the plates preferably one of the absorbers 22, 24 is biased with a positive voltage relative to the ground and the other absorbers is biased with a negative voltage relative to the ground to create a low-voltage difference between the plates. For the purposes of calibration and data gathering, a voltage of +3 volts was applied to the electrical leads 42 to the first absorber 22 and a voltage of −3 volts was applied to the electrical leads 44 to the second absorber 24. In this preferred embodiment, the plates 22, 24 are immersed in the gas atmosphere, preferably an inert gas such as helium. The intensive particle beam crossing the space between the plates 22, 24 ionizes the gas, thus producing a conductivity path between the plates. The applied potential difference between the plates causes electric current to flow in the space region between the plates traversed by the beam. Depending on the beam transverse coordinates, the balance of the horizontal and vertical currents read from the plates will correspond to the position of beam center. The beam position detector 20 collects and processes the information from each of the current monitors 30, 32, 34, 36 and each of the voltage monitors 38, 40. In an especially preferred method of viewing the output of the beam position detector 20, a microprocessor is used to convert the outputs of the current and voltage monitors to a representation of the position of the particle beam path 26 on a two-coordinate grid. In an alternate embodiment, the beam position can be determined even if the plates are immersed in a vacuum.

Figure 2:
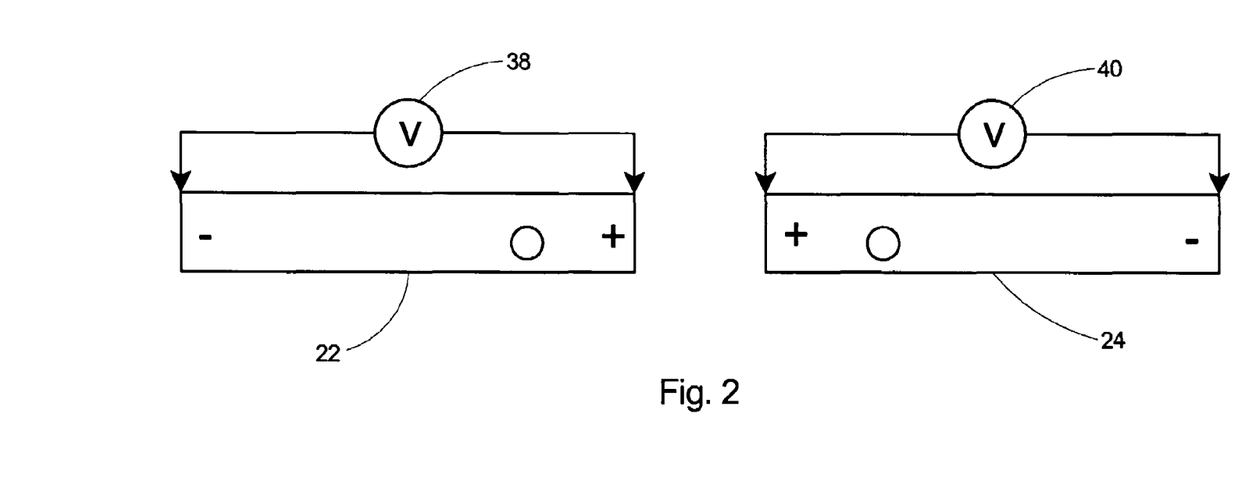
FIG. 2 is a schematic depicting the wiring connections for a voltage measurement across each of the absorbers of FIG. 1.
Figure 3:
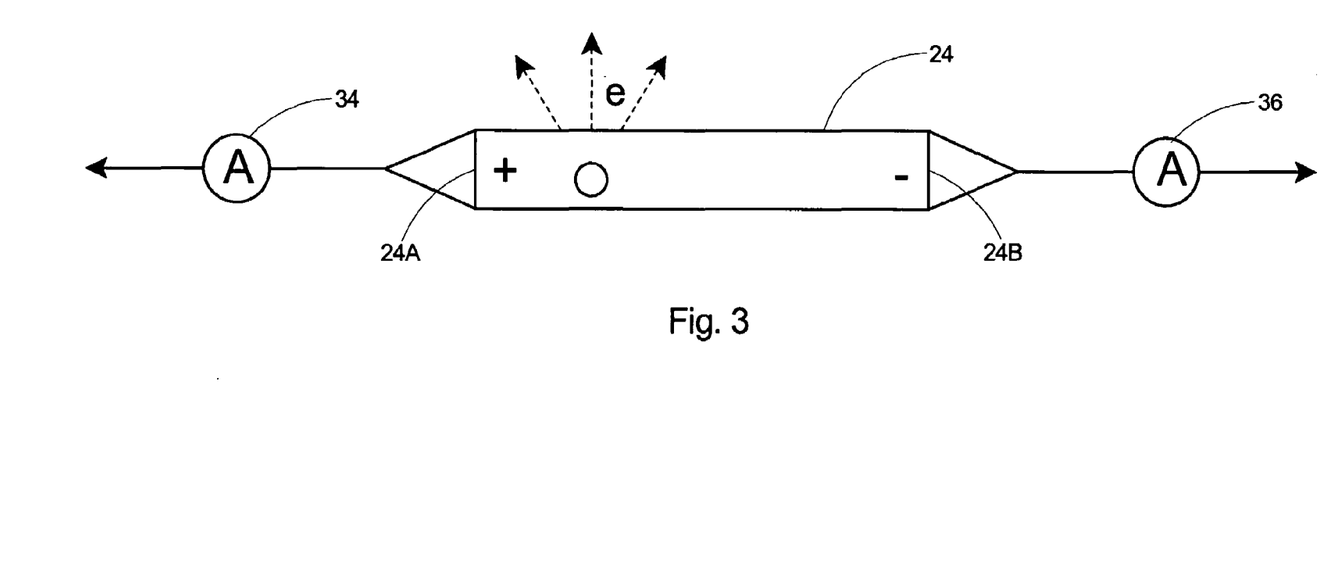
FIG. 3 is a schematic depicting the wiring connections for a current measurement at each end of one of the absorbers of FIG. 1.

Referring to the schematics of FIGS. 2 and 3, the voltage is measured across the absorbers 22, 24 and the current is measured at the ends of the absorbers 22, 24. The voltage meters 38, 40 measure the electric potential generated in each plate 22, 24 in the presence of a temperature gradient caused by the incident particle beam 26. The voltage readout shows a good correlation with the beam position at each plate 22, 24. The balance of the currents are read at the plate corners to characterize the beam position. FIG. 3 depicts the second absorber 24 with current monitors 34, 36 at the two ends 24A and 24B. Electrons are knocked out of the plates at a given rate depending on the beam current. This rate is typically 10 nA per 1 µA beam. The currents are all equal to zero when there is no beam incident upon the plates. The currents are all non-zero and equal if the beam striking the plates is small and symmetrical and hits exactly at the middle of the plates. When the beam moves toward one end of a plate, the current readings increase from that end of the plate and decrease at the opposite end of the plate. By monitoring the balance of currents read at the plate ends, the beam position can be measured.

Referring to FIG. 1, two currents 13, 14, are read from the ends 22A, 22B of the first or vertical absorber 22, two currents 11, 12, are read from the ends 24A, 24B of the second or horizontal absorber 24, and one voltage across each absorber for a total of 6 readings in all. The vertical 22 and horizontal 24 absorbers are biased plus or minus 3 volts relative to the ground to create a low-voltage difference between the plates. Beam ionization in helium gas creates an electrical "short" between the plates, allowing the coordinate readout. Balances of currents from the ends of the vertical 22 and horizontal 24 plates determine the coordinates. Mathematically, in the first approximation, the x and y coordinates are determined by the following formulas:

$$X = C_x(I_1 - I_2)/(I_1 + I_2) \qquad (1)$$

$$Y = C_y(I_3 - I_4)/(I_3 + I_4) \qquad (2)$$

where $I_1$, and $I_2$ are the currents read at the ends of the vertical absorber 22, $I_3$ and $I_4$ are the currents read at the ends of the horizontal absorber 24, and $C_x$ and $C_y$ are calibration coefficients that convert current balance readings into coordinates. $C_x$ and $C_y$ are determined in reference calibration runs with known beam positions.

The balance of the currents from the end of the vertical plate 22 determine the Y coordinate and the balance of the currents from the end of the horizontal plate 24 determine the X coordinate. The voltage readouts V are used to check the consistency of the measured currents or can be used to set an alarm signal or to lock the beam in the center position.

The absorbers 22, 24 are preferably formed of thermo-resistive material. An especially preferred thermo-resistive material of construction for the absorbers is chemical vapor deposition (CVD) silicon carbide (SiC). CVD SiC is a chemically inert, extremely radiation-hard, thermo-resistive semiconductor capable of withstanding working temperatures up to 2000 degrees Kelvin, with its electrical resistivity very sensitive to temperature. The good thermoconductivity of CVD SiC enables it to be used in high-current particle beams.

The beam position detector 20 of FIG. 1 consists of two CVD SiC plates 22, 24 positioned orthogonal to the beam direction or path 26, one vertically 22 and one horizontally 24. The width of the plates 22, 24 would correspond to the designed area on the dump where the beam must be directed. The correctly positioned high-energy charged particle beam would cause a measurable temperature increase in both plates and a misdirected beam would be indicated by a missing signal in one or both of the plates.

FIGS. 4-9 present the calibration data obtained on the prototype Beam Position Detector (BPD) device corresponding to the preferred embodiment shown in FIG. 1, set up inside the electron beam line of an electron accelerator at the vicinity of the beam dump. The conventional Beam Position Monitors (BPMs) were installed approximately 30 meters upstream from the BPD and a few meters upstream of the relatively thick experimental target. The BPMs were thus used to measure the position of the beam prior to the thick helium target, where the quality is good and a conventional beam position monitor is adequate. The quality focused electron beam with energies from 1 to 5 GeV and beam currents in the range of 1 to 120 µA, with transverse dimensions of the order of 0.1 mm by 0.1 mm at the target, was dispersed to the transverse size of about 1 cm by 1 cm at the BPM position by scattering in the target. The calibrations were performed at a beam current of 30 µA. The symbols in the plots represent a series of measurements, one measurement every 10 seconds. The resultant BPM data is used to project the beam position to the place where the BPD is installed, assuming there is no non-linear beam deflection by magnetic fields around the beam line. The correlation of BPD and BPM readings is clearly seen.

Figure 4:
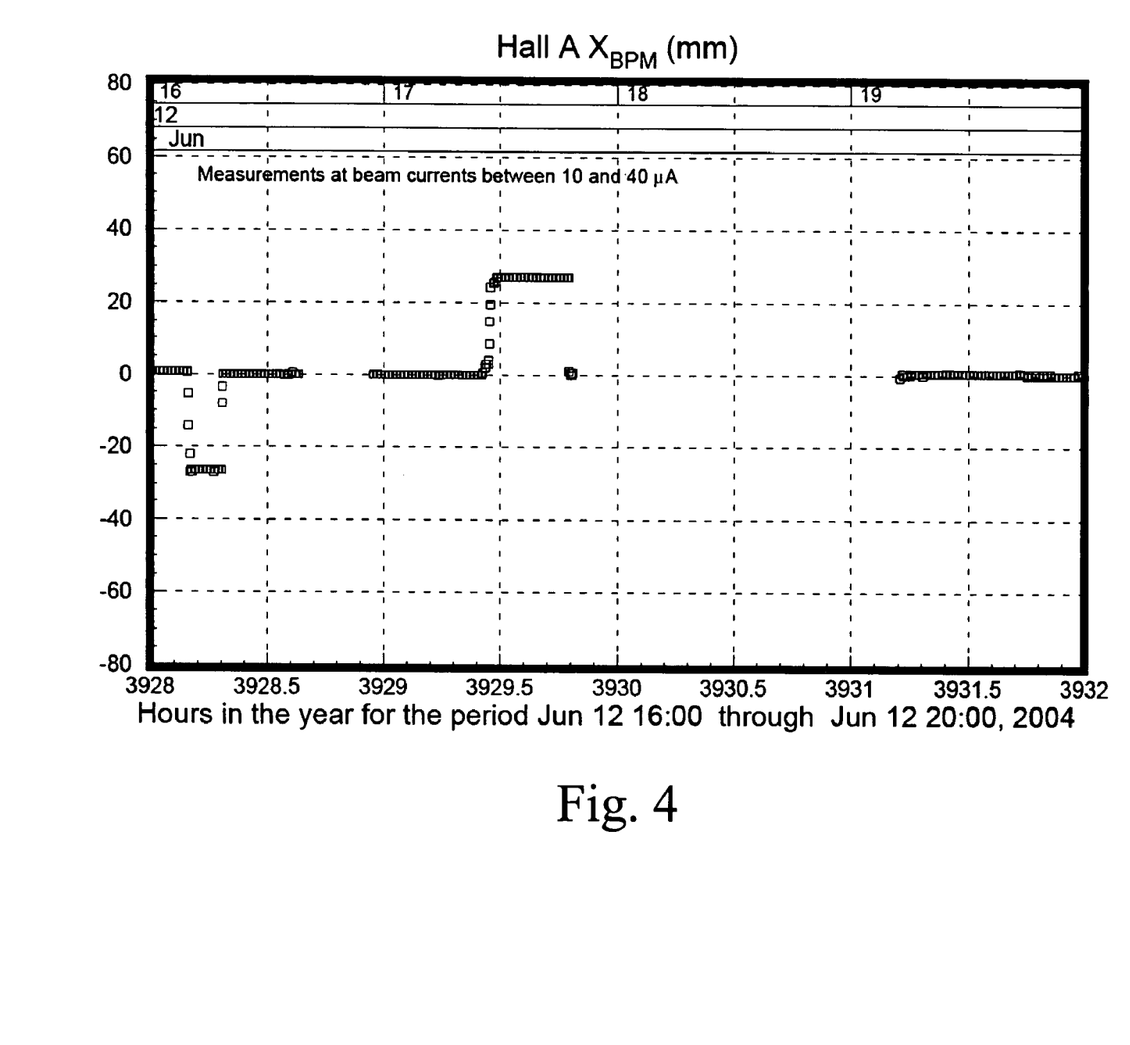
FIG. 4 is a plot of $X_{BPM}$, the beam x-coordinate extrapolated from a conventional beam position monitor (BPM) and projected to the position of the BPD, versus time during calibration of the beam position detector of FIG. 1.
Figure 5:
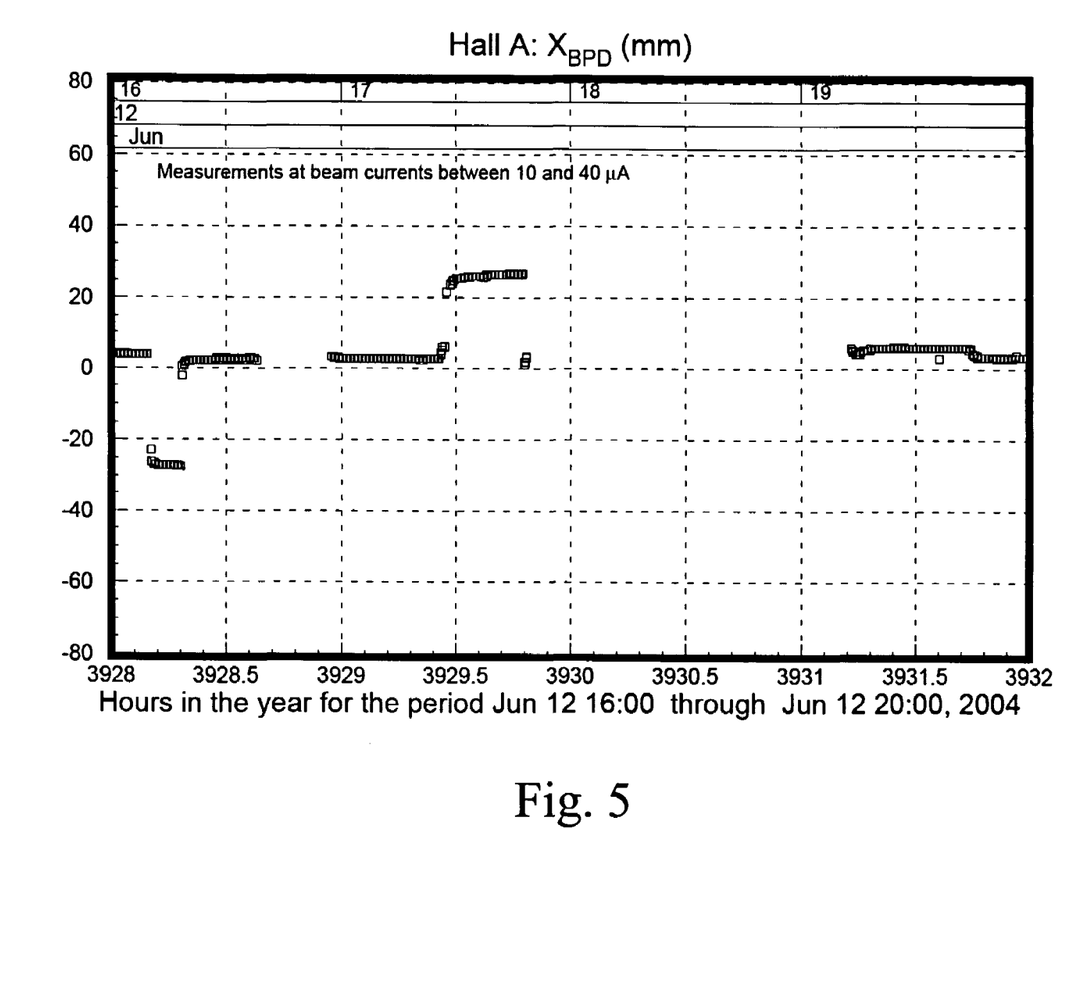
FIG. 5 is a plot of $X_{BPD}$, beam x-coordinate calculated using the balance of currents from the beam position detector (BPD) of FIG. 1, versus time during calibration.
Figure 6:
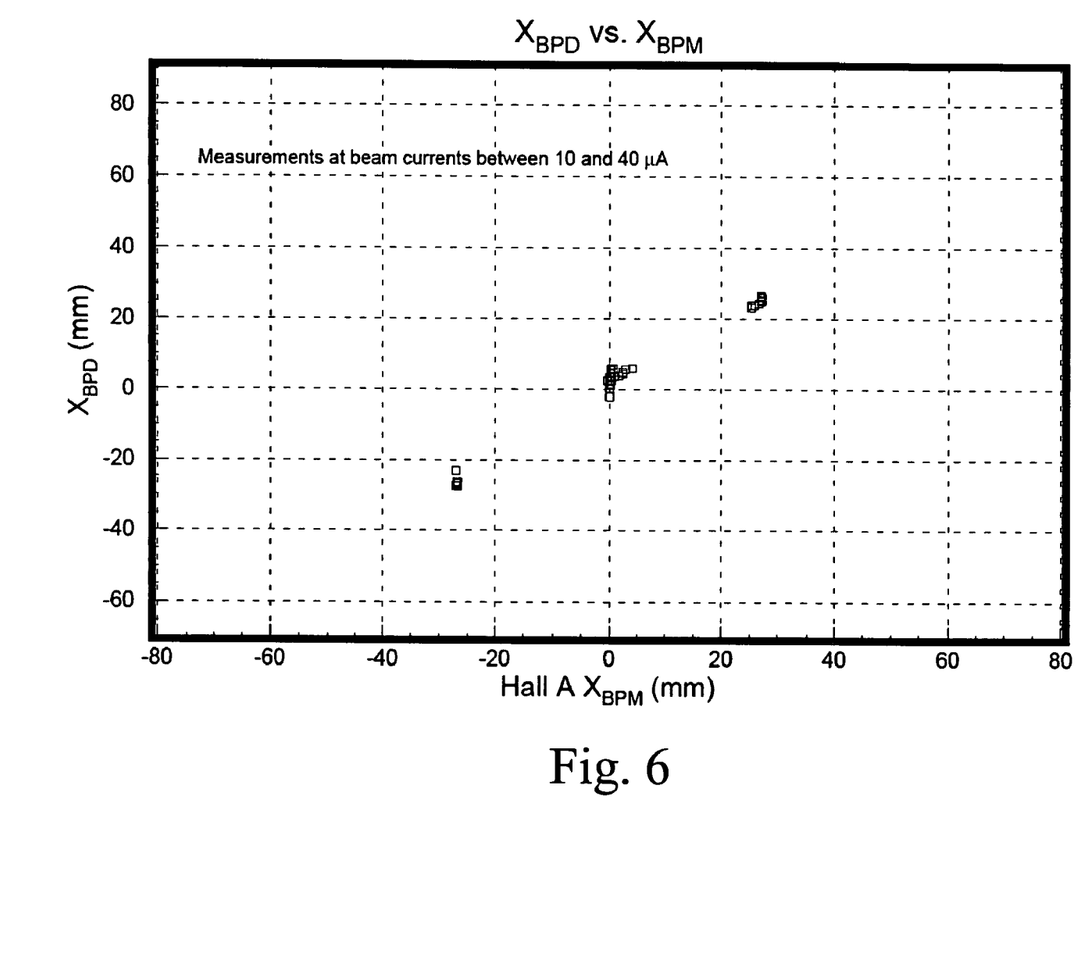
FIG. 6 is a scatter plot of $X_{BPD}$ versus $X_{BPM}$.

FIG. 4 depicts a plot of the x-coordinate of the conventional beam position monitor ($X_{BPM}$) projected to the location of the beam position detector versus time. FIG. 5 is a plot of the x-coordinate output of the beam position detector ($X_{BPD}$) of FIG. 1 versus time for the same time frame studied in FIG. 4. A scatter plot was then made in FIG. 6 plotting $X_{BPD}$ versus $X_{BPM}$.

Figure 7:
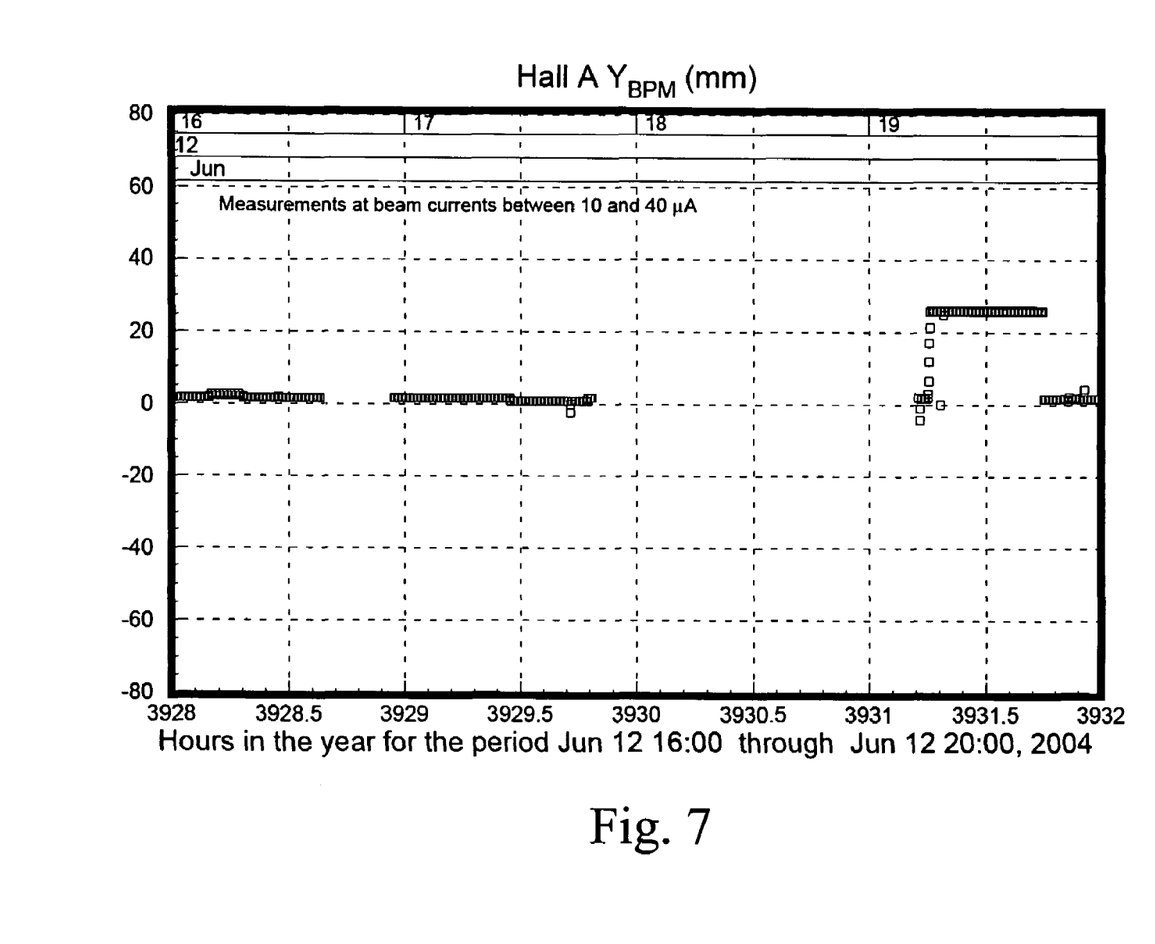
FIG. 7 is a plot of $Y_{BPM}$, the beam y-coordinate extrapolated from a conventional beam position monitor and projected to the position of the BPD, versus time during calibration of the beam position detector of FIG. 1.
Figure 8:
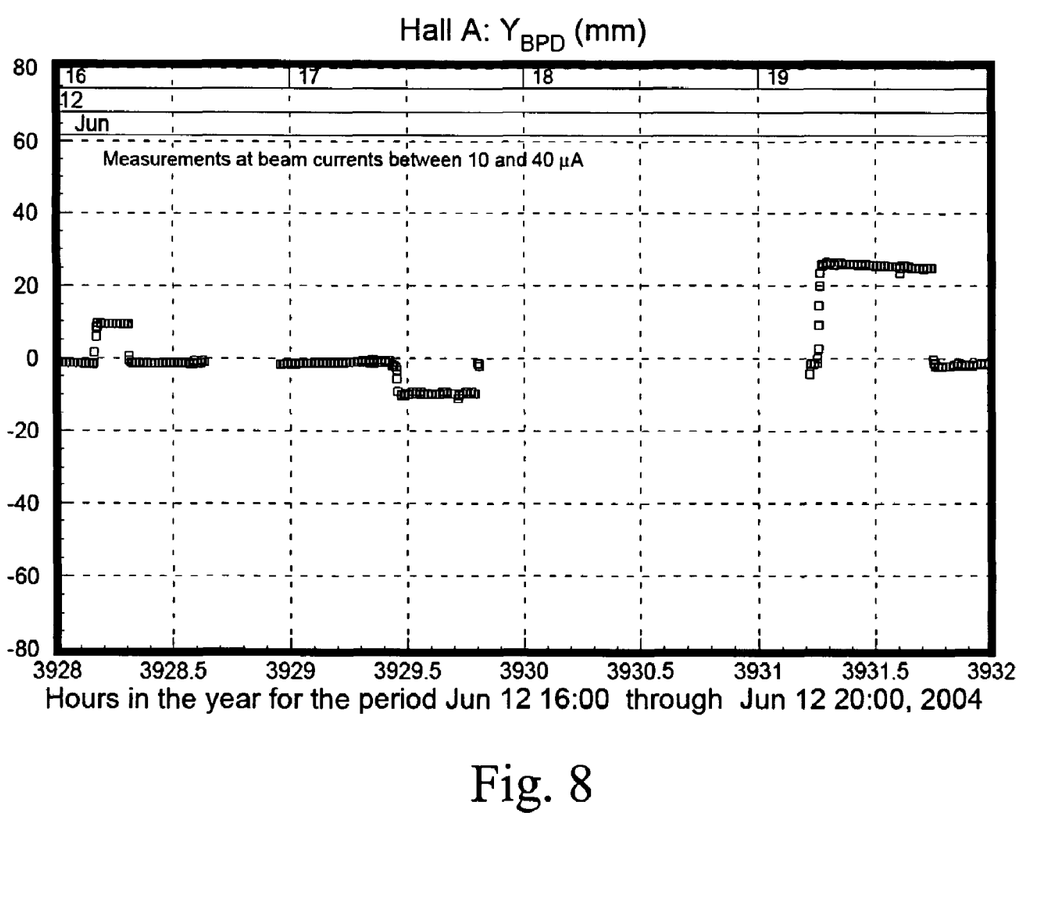
FIG. 8 is a plot of $Y_{BPD}$, beam y-coordinate calculated using the balance of currents from the beam position detector of FIG. 1, versus time during calibration.
Figure 9:
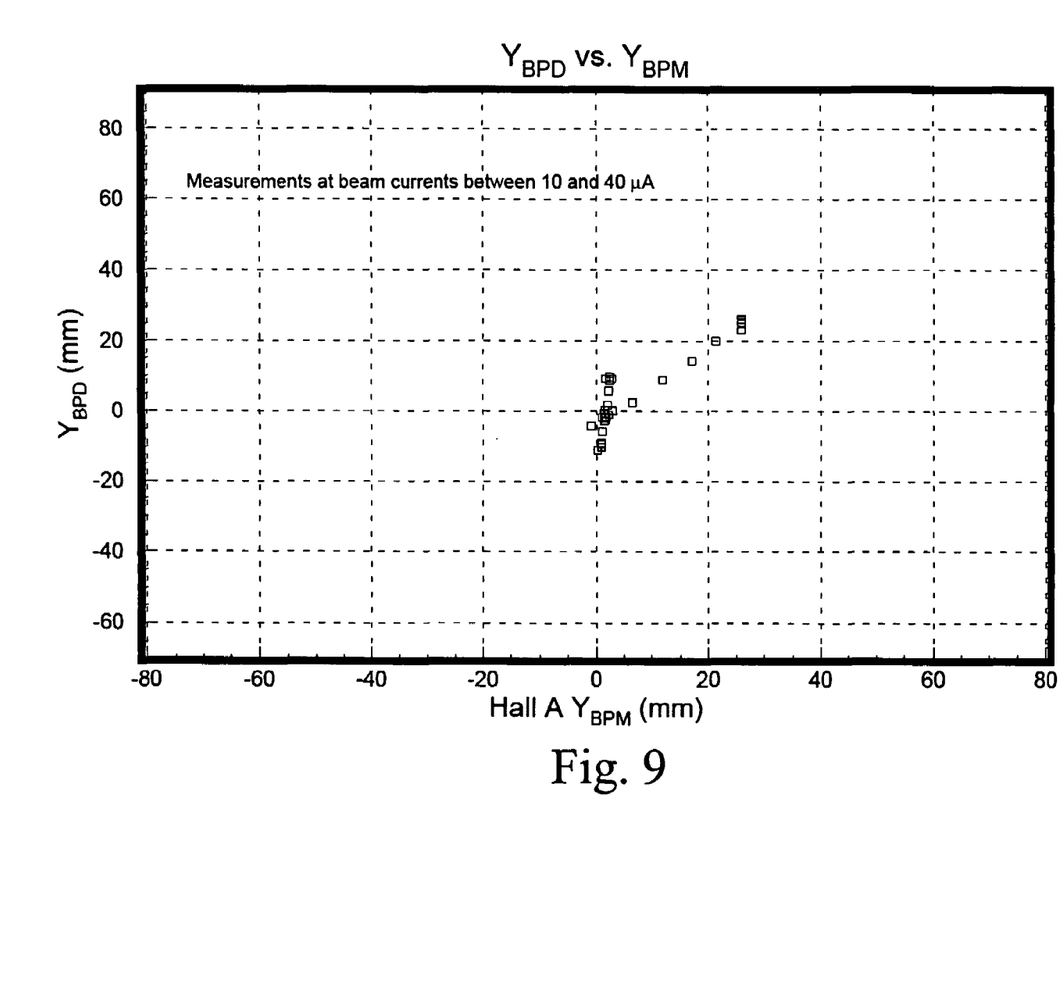
FIG. 9 is a scatter plot of $Y_{BPD}$ versus $Y_{BPM}$.

FIG. 7 is a plot of the y-coordinate output of the conventional beam position monitor ($Y_{BPM}$) projected to the location of the beam position detector versus time. FIG. 8 is a plot of the y-coordinate output of the beam position detector ($Y_{BPD}$) of FIG. 1 versus time for the same time frame studied in FIG. 7. FIG. 9 is a scatter plot of $Y_{BPD}$ versus $Y_{BPM}$.

As previously stated, the BPM is used to measure the position of the beam prior to the target, at a point where the quality of the beam is good. $X_{BPM}$ and $Y_{BPM}$ are therefore extrapolated to the BPD position using BPM readings. $X_{BPD}$ is calculated using the balance of currents from the first absorber plate 22 of the BPD of FIG. 1. $Y_{BPD}$ is calculated using the balance of currents from the second absorber plate 24 of the BPD of FIG. 1. The plot of $X_{BPD}$ versus $X_{BPM}$ and the plot of $Y_{BPD}$ versus $Y_{BPM}$ show clear correlation.

Figure 11:
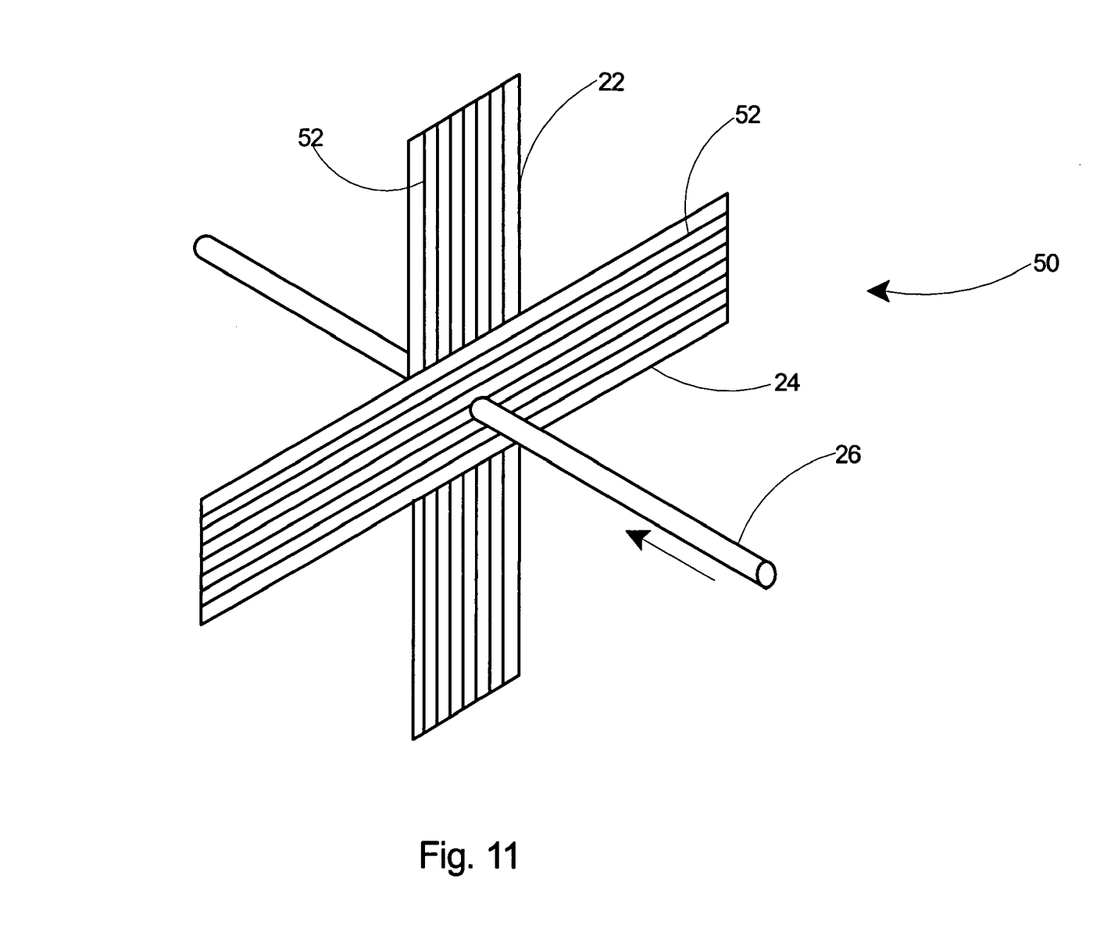
FIG. 11 is a perspective view of another alternate embodiment of a beam position detector for providing more detailed information on the beam size and profile by the use of sets of thin parallel metallic conductors deposited on the plates.

With reference to FIG. 11, a first alternate embodiment of the beam position monitor 50 includes sets of thin parallel metallic conductors 52 deposited on the plates 22, 24 to provide more detailed information on the beam size and profile. The electrical resistance of the sets of thin parallel metallic conductors would be much smaller than the resistance of the plate itself between the two conductors 52. A voltage is applied between the first and the last conductor on a plate to create a voltage distribution across the plate, which is then measured at the ends of the conductors. Directing a high-energy particle beam on the plates 22, 24 between two conductors will cause local heating of the plate thereby changing the resistance, and, correspondingly, the measured voltage between the conductors, thus locating the position of the beam across the plate. The pattern of changed voltage distribution measured at every conductor can be used to evaluate the beam profile across the plate. Using two orthogonal plates, one can measure the detailed beam distribution in horizontal and vertical directions.

Figure 10:
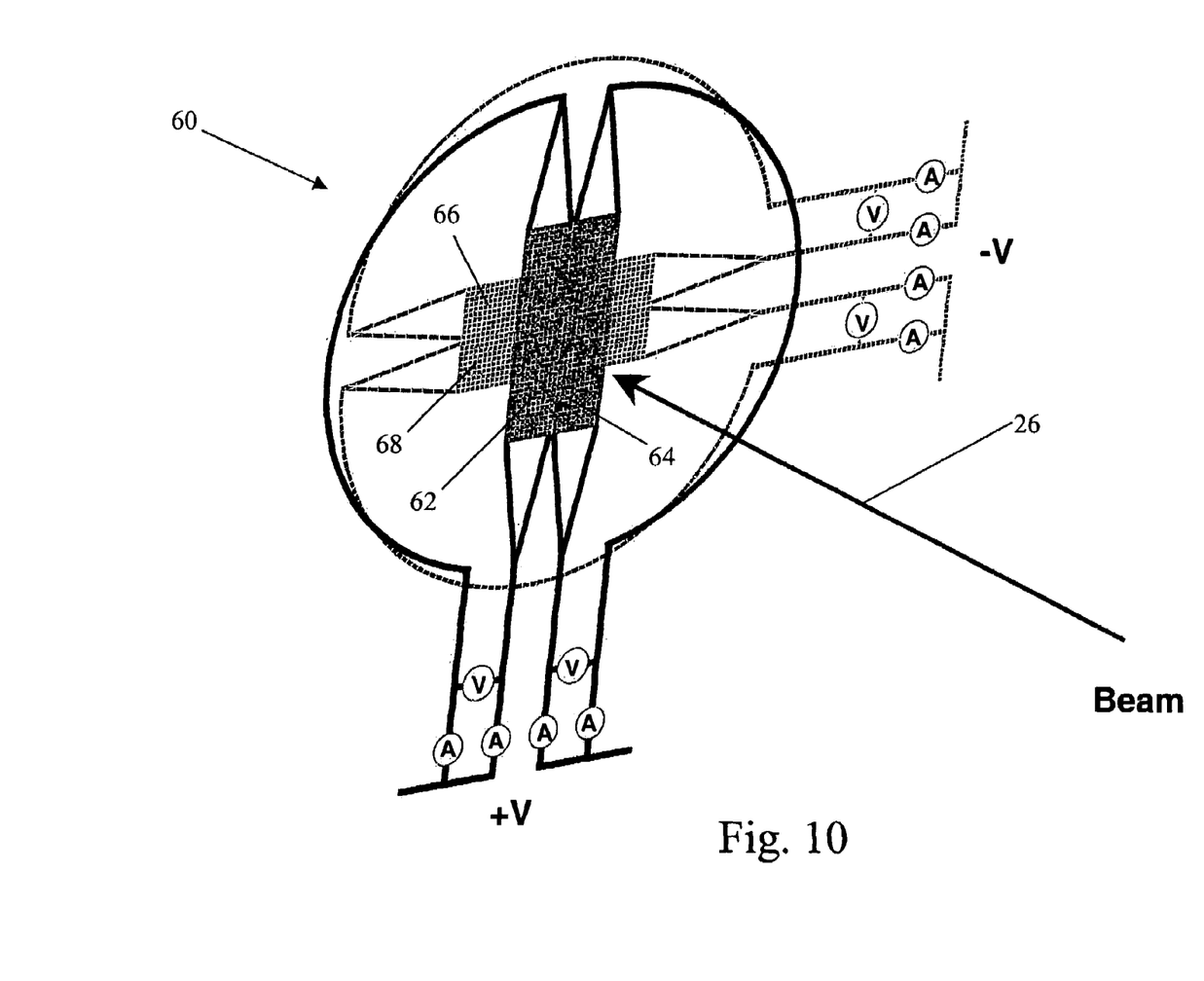
FIG. 10 is a perspective view of an alternate embodiment of a beam position detector according to the present invention using four resistive absorbers.

Referring to FIG. 10 there is depicted a second alternate embodiment of a particle beam position monitor 60 according to the present invention. The monitor 60 includes four resistive absorbers set across the beam path 26. Two absorbers 62, 64 are positioned orthogonal and vertically with respect to the beam path 26 and two absorbers 66, 68 are positioned orthogonal and horizontally with respect to the beam path 26. Each absorber provides information about a slice of the beam profile. The full beam profile can be obtained using the combined information from all of the absorbers.

Another alternate embodiment of the beam position detector, not depicted herein, would include similar absorbers made of a transparent thermo-resistive glass material and be used to monitor the position of a powerful laser beam. A small fraction of the laser beam power dissipated in the glass absorber will cause local heating and thus a measurable resistance change.

The preferred embodiment of the beam position monitor 20 shown in FIG. 1 features a simplified construction, using one vertical 22 and one horizontal 24 plate. The CVD SiC plates are preferably 50 mm width, 200 mm length, and 0.25 mm thick. Using the CVD SiC provides several advantages, including thermoconductivity comparable with copper and beryllium, high stiffness, machinability, stable up to 2000 degrees Kelvin, a resistance of between 200 and 600 kohm measured across the long ends of the rectangular plates, and high resistance response with resistivity falling 100 times in the temperature range of 50 to 500 degrees C. The CVD SiC plates are also resistant to degradation due to plasmas, acids, bases, and radiation.

Experimentation with different experimental targets shows that the response from the BPD may depend on the target, and therefore each target must be calibrated separately. Different targets scatter the beam differently, producing different beam spot sizes and generating different numbers of secondary electrons, which go in the line along with the beam, with smaller energies. The magnetic fields along the beamline deviate these lower energy electrons more easily than the main beam, thus producing non-symmetric beam image at the BPD. Effectively, it may shift the BPD readout along the major direction of the deviation.

Alternatively, the absorbers could be constructed of wires constructed of CVD SiC. The wires would be strung parallel to one another to form a rectangular shape, with the wires running longitudinally along the rectangular-shaped absorber. Each wire, if hit by a particle beam, would have its temperature elevated, thus allowing it to be detected by measuring its resistance.

Having thus described the invention with reference to a preferred embodiment, it is to be understood that the invention is not so limited by the description herein but is defined as follows by the appended claims.

What is claimed is:

1. A beam position detector for use with a high energy accelerator particle beam having a path comprising:
   a first and second absorber of thermo-resistive material intersecting said path;
   said first absorber positioned vertically and orthogonal with respect to said path;
   said second absorber positioned downstream of said first absorber and horizontally and orthogonal with respect to said path;
   a gap between said absorbers;
   said absorbers detecting a localized current caused by either knock-out electrons in vacuum or ionization current in gas and induced by a voltage difference between said absorbers;
   a current monitor at each end of each of said absorbers;
   a voltage monitor across each of said absorbers; and
   a processor for converting the outputs of said current and voltage monitors to a representation of the position of said particle beam.

2. The beam position detector of claim 1 wherein said first and second absorbers are rectangular plates.

3. The beam position detector of claim 2 wherein said plates are constructed of silicon carbide.

4. The beam position detector of claim 3 wherein said plates constructed of silicon carbide are produced by a chemical vapor deposition process.

5. The beam position detector of claim 4 wherein said plates are 0.25 mm thick for a particle beam having a current of between 5 and 200 Lamps.

6. The beam position detector of claim 5 wherein said silicon carbide plates have an electrical resistance of 200 to 600 kohms measured longitudinally across said rectangular plates.

7. The beam position detector of claim 2 wherein
   each of said plates includes four corners;
   said current monitor at the ends of said plates includes a current monitor reading the current at each of said corners; and
   said representation of the position of said particle is determined from the balance of the currents read at said corners of said plates.

8. The beam position detector of claim 2 wherein
   each of said plates includes two ends;
   said current monitor at the ends of said plates includes a first current monitor reading the current at a first end of said plates and a second current monitor reading the current at a second end of said plates; and
   said representation of the position of said particle is determined from the balance of the currents read at said ends of said plates.

9. The beam position detector of claim 8 wherein said voltage monitor across each of said plates measures the consistency of the currents read at said corners of said plates.

10. The beam position detector of claim 2 wherein one of said first and second absorbers is biased with a positive voltage relative to the ground and the other of said first and second absorbers is biased with a negative voltage relative to the ground to create a low-voltage difference between the plates.

11. The beam position detector of claim 2 wherein said beam position detector provides the position, size, shape, and intensity of said particle beam.

12. The beam position detector of claim 1 wherein said first and second absorbers include parallel wires strung longitudinally to form a rectangular shape.

13. The beam position detector of claim 1 wherein said absorbers are immersed in a vacuum.

14. The beam position detector of claim 1 wherein said absorbers are immersed in an inert gas.

15. The beam position detector of claim 14 wherein said inert gas is helium.

16. A method of monitoring a high energy accelerator particle beam having a path comprising the steps of:
   providing a first and second absorber of thermo-resistive material intersecting said path;
   positioning said first absorber vertically and orthogonal with respect to said path;
   positioning said second absorber downstream of said first absorber and horizontally and orthogonal with respect to said path thereby forming a gap between said absorbers;
   providing a current monitor at each end of each of said absorbers for detecting a localized current caused by either knock-out electrons in vacuum or ionization current in gas and induced by a voltage difference between said absorbers;
   providing a voltage monitor across each of said absorbers;
   providing a processor for converting the outputs of said current and voltage monitors to a representation of the position of said particle beam on a two-coordinate graph; and
   measuring the position, size, shape, and intensity of said particle beam by the use of said two-coordinate graph.

17. The beam position detector of claim 16 wherein said first and second absorbers are rectangular plates.

18. The beam position detector of claim 16 wherein said plates are constructed of silicon carbide produced by a process of chemical vapor deposition.

19. The beam position detector of claim 18 wherein said plates are 0.25 mm thick for a particle beam having a current of between 5 and 200 μamps.

20. The beam position detector of claim 19 wherein said silicon carbide plates are thermo-resistive with an electrical resistance of 200 to 600 kohms measured longitudinally across said rectangular plates.

* * * * *